United States Patent
Kim et al.

(10) Patent No.: US 8,277,795 B2
(45) Date of Patent: Oct. 2, 2012

(54) METHODS AND COMPOSITIONS FOR TREATING MOTOR NEURON DISEASES COMPRISING MESENCHYMAL STEM CELLS

(75) Inventors: Hee Tae Kim, Seoul (KR); Kyung Suk Kim, Seoul (KR); Seung Hyun Kim, Seoul (KR); Young Gyu Chai, Seoul (KR); Seong Ho Koh, Seongnam-si (KR); Hyun Young Kim, Hanam-si (KR); Mi Ran Choi, Seoul (KR); Ji-Yoon Park, Goyang-si (KR); Kyoung Hwa Jung, Gimcheon-si (KR)

(73) Assignee: Corestem Co., Ltd., Chungcheongbuk-do (KR)

( * ) Notice: Subject to any disclaimer, the term of this patent is extended or adjusted under 35 U.S.C. 154(b) by 920 days.

(21) Appl. No.: 12/302,161

(22) PCT Filed: Nov. 28, 2006

(86) PCT No.: PCT/KR2006/005066
§ 371 (c)(1),
(2), (4) Date: Nov. 24, 2008

(87) PCT Pub. No.: WO2007/136156
PCT Pub. Date: Nov. 29, 2007

(65) Prior Publication Data
US 2009/0186005 A1   Jul. 23, 2009

(30) Foreign Application Priority Data
May 24, 2006 (KR) .......................... 10-2006-0046695

(51) Int. Cl.
*A01N 63/00* (2006.01)

(52) U.S. Cl. ........................................ 424/93.1; 435/372
(58) Field of Classification Search ........................ None
See application file for complete search history.

(56) References Cited

FOREIGN PATENT DOCUMENTS

WO   02/086108 A1   10/2002
WO   2004/016779 A1   2/2004

OTHER PUBLICATIONS

Janson et al. Human Intrathecal Transplantation of Peripheral Blood Stem Cells in Amyotrophic Lateral Sclerosis. J. Hemato. Stem Cell Res., 2001, vol. 10, pp. 913-915.*
Mazzini et al. Stem cell therapy in amyotrophic lateral sclerosis: A methodological approach in humans. ALS, 2003, vol. 4, pp. 158-161.*
Brugman et al. Primary Lateral Sclerosis. Orphanet Encylopedia, 2004, http://www.orpha.net/data/patho/GB/uk-PLS.pdf.*
Pittenger et al. Mesenchymal Stem Cells and Their Potential as Cardiac Therapeutics. Circulation Res., 2004, vol. 95, pp. 9-20.*
Zhao, et al., "Human Bone Marrow Stem Cells Exhibit Neural Phenotypes and Ameliorate Neurological Deficits after Grafting into the Ischemic Brains of Rats," Experimental Neurology, 174, 11-20 (2002).

* cited by examiner

*Primary Examiner* — Deborah Crouch
(74) *Attorney, Agent, or Firm* — Sughrue Mion, PLLC

(57) ABSTRACT

Disclosed herein are a composition for treating motor neuron diseases, particularly amyotrophic lateral sclerosis (ALS), using mesenchymal stem cells, and a method for treating motor neuron diseases using the composition. The composition and treatment method can provide effective therapy for motor neuron diseases, particularly for amyotrophic lateral sclerosis (ALS).

4 Claims, 1 Drawing Sheet

[Fig. 1]
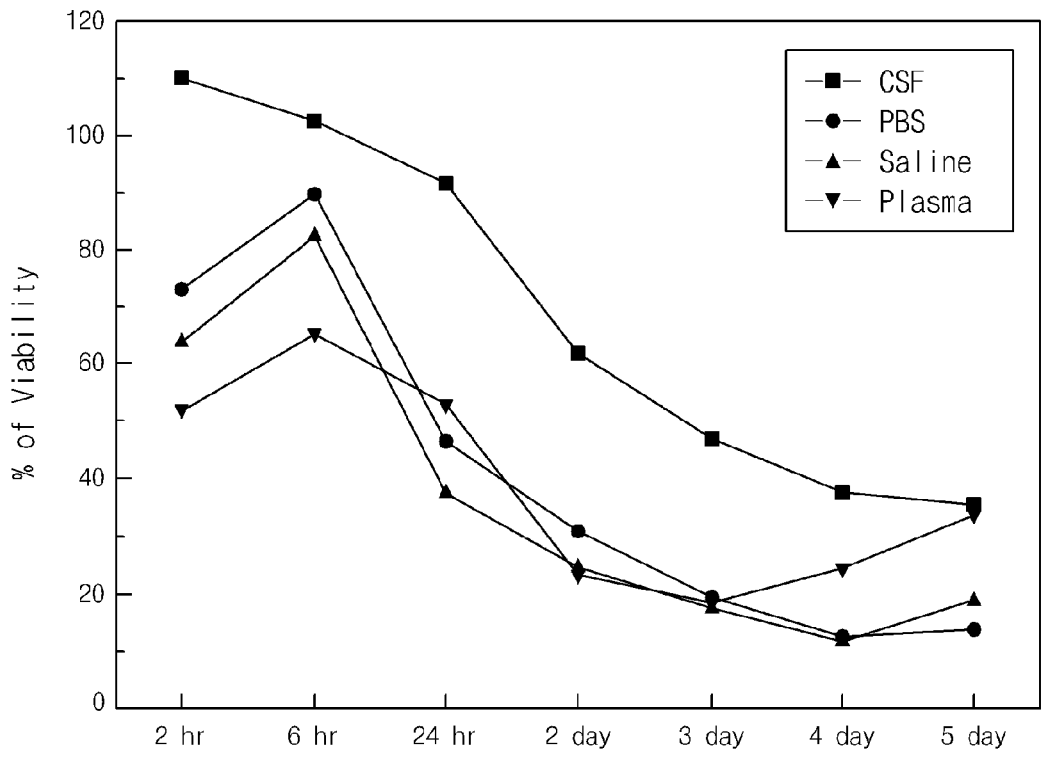
[Fig. 2]
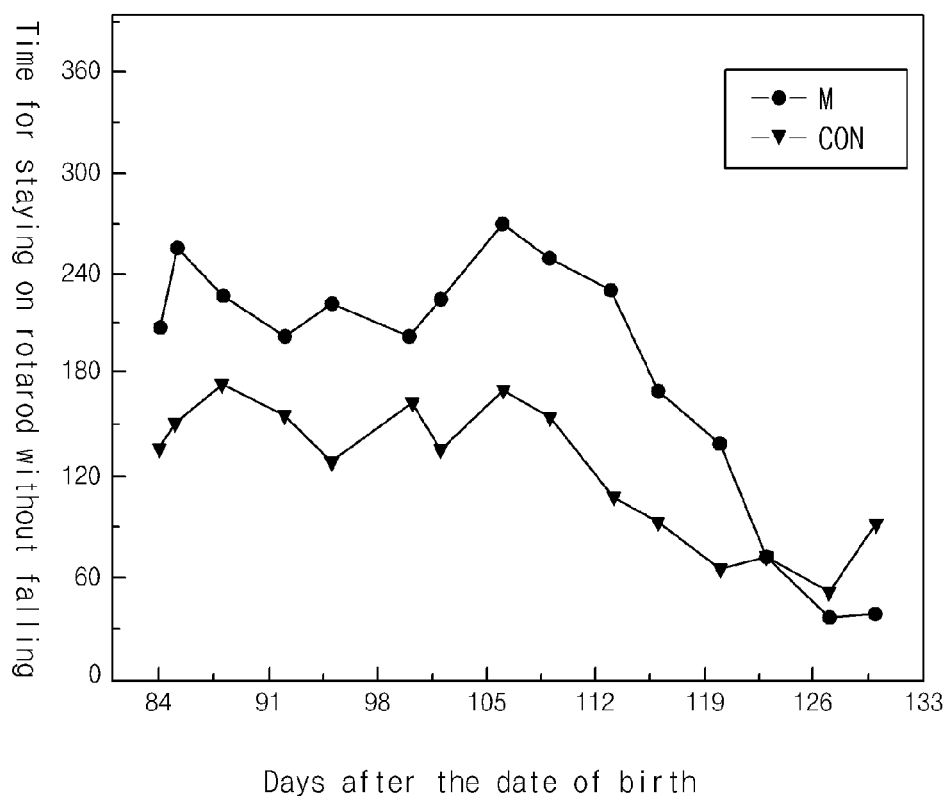

METHODS AND COMPOSITIONS FOR TREATING MOTOR NEURON DISEASES COMPRISING MESENCHYMAL STEM CELLS

This is a national stage application under 35 U.S.C. §371 of PCT/KR2006/005066 filed on Nov. 28, 2006, which claims priority from Korean patent application 10-2006-0046695 filed on May 24, 2006, all of which are incorporated herein by reference.

TECHNICAL FIELD

The present invention relates to a composition for treating motor neuron diseases (MNDs), particularly amyotrophic lateral sclerosis (ALS; also known as Lou Gehrig's disease), using mesenchymal stem cells, and a method therefor.

BACKGROUND ART

Motor neuron diseases (MNDs) are diseases which lead to impairment of the motor nerve functions due to the loss of motor neuron cells and degenerative changes in the motor pathways of the central nervous system, and are essentially different from neurodegenerative diseases such as Parkinson's disease, Alzheimer's disease, and cerebellar atrophy and the like, because they involve damages to other nerve cells. These MNDs include, in addition to amyotrophic lateral sclerosis (also known as Lou Gehrig's disease), diseases which are classified into primary lateral sclerosis (PLS) affecting only upper motor neurons, progressive muscular atrophy (PMA) affecting only lower motor neurons, progressive bulbar palsy (PBP) affecting lower motor neurons of the brain stem, and the like.

Amyotrophic lateral sclerosis (ALS; also known as Lou Gehrig's disease) is one of the motor neuron diseases (MNDs), and is a neurological disease which selectively affects motor neurons only, although the pathological mechanism is still not known clearly (Haverkamp L J et al., Validation of a scoring system and a model for survival prediction Brain 1995; 118:707-19., Caroscio J T et al., Neurol Clin 1987; 5:1-9). ALS causes, from a pathological aspect, the loss of pyramidal cells in the cerebral motor cortex (i.e., giant Betz cells), anterior spinal motor neurons and brain stem motor neurons, and degeneration thereof into pyramidal cells; while ALS shows, from a clinical aspect, both upper motor neurons and lower motor neurons signs, and shows rapid clinical deterioration after onset of the disease, thus leading to death within a few years. An incidence rate of ALS corresponding to 1 to 2 persons and a prevalence rate corresponding to 4 to 6 persons, out of a population of 100,000 are reported, while the incidence rate is 1.5-fold higher in men than in women, but the incidence rates become similar to each other at an age of from 50's to 60's.

The only safe drug used for treating ALS is riluzole, which has an antagonistic effect against glutamate, and has been approved by the US Food and Drug Administration (FDA) for commercialization. However, this drug shows unsatisfactory efficacy, which means currently there is no definite therapy for ALS that can improve rapidly deteriorating clinical conditions.

Recently, various attempts to treat the nerve system disorders, including ALS, have been conducted using stem cells. For example, Korean Patent Application Publication No. 2005-0012208 discloses that mesenchymal stem cells are cultured in a medium containing an epidermal growth factor and a hepatocyte growth factor, and then differentiated and expanded into nerve cells, which are in turn transplanted into a patient to treat a nerve system disease. However, the method as disclosed in this patent application is a method for transplanting the nerve cells, which had been differentiated from mesenchymal stem cells, and the method requires a complex process and a long period of time to induce their differentiation In this regard, the present inventors have conducted research on a new method for treating motor neuron diseases, particularly ALS, and found that when mesenchymal stem cells (MSCs) of their own are isolated and expanded ex vivo to obtain a sufficient number of cells, and the cells are employed for cell therapy in animal models as well as patients with ALS diseases, rapid clinical deterioration is mitigated in the patients, and a significant therapeutic effect is obtained, thereby completing the present invention.

DISCLOSURE OF INVENTION

Technical Solution

It is an object of the present invention to provide a composition for treating motor neuron diseases, particularly ALS, comprising mesenchymal stem cells.

It is another object of the present invention to provide a method for treating motor neuron diseases, particularly ALS, by administering the composition to an individual.

BRIEF DESCRIPTION OF THE DRAWINGS

FIG. 1 is a graph showing the results of the cell viability of the MSCs which were isolated from a patient with ALS and suspended in various solutions such as PBS, normal saline, plasma, and cerebrospinal fluid (CSF), and then cultured them ex vivo; and FIG. 2 is a graph showing the treatment effect of MSCs after treating a mouse model of amyotrophic lateral sclerosis (human-SOD1 mutant transgenic mouse model) with the MSCs isolated from a patient with ALS. The MSCs treated group (—●—) showed 30% significant difference from the control group (Con) (—▼—).

BEST MODE FOR CARRYING OUT THE INVENTION

According to an embodiment, the present invention relates to a composition for treating motor neuron diseases using mesenchymal stem cells.

As used herein, the term "mesenchymal stem cells (MSCs)" refer to pluripotent progenitors for bone, cartilage, fat, tendon, nerve tissues, fibroblasts, and muscle cells before being differentiated into the cells of specific organs. These mesenchymal stem cells can be isolated and purified from tissues such as bone marrow, peripheral nerve blood, umbilical cord blood, periosteum, dermis, and other tissues of mesodermal origins.

The human mesenchymal stem cells can be obtained, for example, from a number of different sources, including plugs of femoral head cancellous bone pieces obtained from patients with degenerative joint disease during hip or knee replacement surgery, and aspirated marrow obtained from normal donors and patients having marrow harvested for future bone marrow transplantation. In specific embodiments, autologous mesenchymal stem cells obtained from a patient with ALS were used. The mesenchymal stem cells are isolated by a number of different mechanical isolation processes depending upon the source of the bone marrow (i.e. the presence of bone chips, peripheral blood, etc.), which are known in the art. The critical step involved in the isolation processes is to use a specially prepared medium containing agents, which allow for not only mesenchymal stem cell growth without differentiation, but also for the direct adherence of only the mesenchymal stem cells to the plastic or glass surface area of the culture dish. By using the medium that allows for the selective attachment of the desired mesenchymal stem cells, which are present in the bone marrow samples in very minute amounts, it is possible to separate the mesenchymal stem cells from the other cells (i.e. red and white blood cells, other differentiated mesenchymal cells, etc.) present in the bone marrow.

As the culture media for culturing the mesenchymal stem cells of the present invention, basal media for cells, such as DMEM (Dulbecco's Modified Eagle's Medium), MEM (Minimal Essential Medium), BME (Basal Medium Eagle), RPMI 1640, F-10, F-12, α-MEM (α-Minimal Essential Medium), G-MEM (Glasgow's Minimal Essential Medium), ISDM (Iscove's Modified Dulbecco's Medium), and MSCGM can be used. Further, a medium further containing growth factors such as insulin (10 ng/ml), hydrocortisone (10 nM), EGF (10 ng/ml), FGF, NGF, and LIF, or sera which are essential for growth, such as fetal bovine serum, horse serum, goat serum, human serum, umbilical cord serum in addition to the basal medium can also be used. In particular, in Examples of the present invention, a large amount of mesenchymal stem cells was obtained by culturing mesenchymal stem cells without differentiation in a culture medium containing human umbilical cord serum which had been developed by the present inventors. The mesenchymal stem cells can be cultured in the medium under the condition of temperature of 36 to 38° C., and 3 to 10% $CO_2$.

The cultured cells express the positive surface markers for the mesenchymal stem cells, such as CD105 (or CD105 (SH2)), CD29, CD44, CD73, and CD166 at 50% or more, preferably 90% or more, and more preferably they express the positive surface markers of CD29, CD44, CD73, and CD105 at 95% or more, and express the negative surface markers such as CD34, CD45, HLA-DR, CD1a, CD4, CD31, and CD80 at 50% or less, preferably 10% or less, and more preferably they express the negative surface markers of CD34, CD45, and HLA-DR at 5% or less.

The isolated and cultured mesenchymal stem cell composition can be administered to an individual after being diluted in a suitable diluent at a concentration of about 0.01 to about $5 \times 10^6$ cells/ml. This diluent is used so as to protect and maintain the cells, and to be able to be transplanted easily into the brain tissues. Examples of the diluent include buffered solutions such as normal saline, PBS, and HBSS, blood plasma, cerebrospinal fluid, and blood components, and preferably normal saline, PBS, HBSS, blood plasma, or cerebrospinal fluid.

The composition of the present invention can further comprise other factors to promote the signal pathways of the mesenchymal stem cells or to promote the differentiation into nerve cells and growth.

The composition of the present invention can be used in a mixture with a pharmaceutically acceptable carrier or excipient, or after being diluted with a diluent. Examples of the suitable carriers, excipients and diluents include lactose, dextrose, sucrose, sorbitol, mannitol, xylitol, maltitol, starch, acacia gum, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oils. In addition, the composition can further comprise a filler, an anti-coagulating agent, a lubricant, a humectant, a perfume, an emulsifier, an antiseptic, or the like, if desired. For the purpose of the present invention, the composition comprising the mesenchymal stem cells refers to both a composition having the mesenchymal stem cells of the present invention diluted with a diluent, and a composition which has been pharmaceutically formulated. For convenience, the composition comprising the mesenchymal stem cells may be simply referred to as mesenchymal stem cells.

The composition of the present invention can be formulated by a method well-known in the art to provide a rapid or sustained release of the active ingredients after being administrated into an individual. The composition may be formulated into a tablet, a powder, a pill, a sachet, an elixir, a suspension, an emulsion, a solution, a syrup, an aerosol, a soft or hard gelatin capsule, a sterilized injectable solution, a sterilized powder, or the like. The composition may be conveniently formulated into a unit dosage form. The composition of the present invention is most preferably an injectable preparation.

The mesenchymal stem cell composition of the present invention can be administered through various administration routes including topical (including buccal, sublingual, dermal, and intraocular), parenteral (including subcutaneous, intradermal, intramuscular, intravascular, and intraarticular), and transdermal administration, and preferably parenteral administration. Most preferable parenteral administration is intrathecal administration. The present inventors have found that the mesenchymal stem cells are very effective for treating motor neuron diseases, particularly ALS, when diluted in cerebrospinal fluid and injected intrathecally. By intrathecal injection of the mesenchymal stem cells, the occurrence of complications such as the risk of infection, and nerve injury can be avoided. Further, by using autologous cerebrospinal fluid, the expected side effects can be minimized, and a non-invasive treatment can be performed advantageously.

The composition of the present invention is administered in a pharmaceutically effective amount. As used herein, the phrase "pharmaceutically effective amount" refers to an amount sufficient to treat a disease. The level of the effective dosage can be determined according to the severity of the disease; the age, weight, health, and sex of a patient; the drug sensitivity in a patient; the administration time, route, and release rate; the treatment duration; or elements including drugs that are blended or simultaneously used with the composition of the present invention, or other elements well-known in the medical field. For example, the dosage of the mesenchymal stem cells varies within a wide range, and is determined according to the requirements of the individuals in specific cases. Generally, in the case of parenteral administration, the mesenchymal stem cells are usually administered in an amount of about 0.01 to about 5,000,000 cells/kg of a body weight of the individual. Further, the composition of the present invention and other motor neuron disease-treating substances known in the art can be simultaneously or sequentially administered to an individual.

As used herein, the phrase "composition comprising mesenchymal stem cells" refers to compositions for treating motor neuron diseases, wherein the motor neuron diseases means amyotrophic lateral sclerosis (ALS), progressive bulbar palsy (PBP), primary lateral sclerosis (PLS), or progressive muscular atrophy (PMA). The composition of the present invention is preferably a composition for treating amyotrophic lateral sclerosis (ALS).

The composition of the present invention is highly effective for the treatment of motor neuron diseases. That is, the composition of the present invention shows enhanced motor ability of mice which had been administered with the composition of the present invention, as compared with mice which had been not administered with the composition of the present invention, with the enhancement approaching 30%. Further, in the clinical experiment, the patients which had been administered with the composition of the present invention showed clinical changes such as remarkable improvement in the phonation, respiration, and deglutition functions, delayed time of maintaining a standing position, and reduced insomnia, and such changes were maintained for a long period of time.

In another embodiment, the present invention relates to a method for treating motor neuron diseases, which comprises a step of administering a composition comprising mesenchymal stem cells for treating motor neuron diseases to an individual.

As used herein, the term "treatment" refers to a means for therapeutic treatment, prevention, or amelioration. Thus, the phrase "a person in need of treatment" encompasses a person who is suffering from a motor nerve disorder or a motor neuron disease, and a person who tries to prevent a motor nerve disorder or a motor neuron disease. As used herein, the term "an individual" refers to any mammal in need of treatment, including a human and non-human primates, domestic animals and livestock, pet or sports animals, for example, dogs, horses, cats, sheep, pigs, and cows.

In one embodiment, the present invention relates to a method for treating motor neuron diseases, comprising the steps of diluting the mesenchymal stem cells with a diluent or formulating the mesenchymal stem cells into a pharmaceutical composition; and administering the composition to an individual in need. In a specific embodiment, the present invention relates to a method for treating motor neuron diseases, comprising the steps of diluting the mesenchymal stem cells with a diluent or formulating the mesenchymal stem cells into a pharmaceutical composition; and parenterally administering the composition to an individual in need. In another specific embodiment, the present invention relates to a method for treating motor neuron diseases, comprising the steps of diluting the mesenchymal stem cells with a diluent or formulating the mesenchymal stem cells into a pharmaceutical composition; and intrathecally administering the composition to an individual in need.

The present inventors have found that the mesenchymal stem cells are very effective for treating motor neuron diseases, particularly ALS, when diluted in cerebrospinal fluid and injected intrathecally. By intrathecal injection of the mesenchymal stem cells, the occurrence of complications such as the risk of infection and nerve injury can be avoided. Further, by using autologous cerebrospinal fluid, the expected side effects can be minimized, and a non-invasive treatment can be performed advantageously.

Hereinbelow, the present invention will be described in detail with reference to the following Examples. These Examples are provided only for the illustrative purpose, and are not constructed to limit the scope of the present invention.

MODE FOR THE INVENTION

Example 1

Criteria for Selection of ALS Patients

The therapeutic effects of the mesenchymal stem cells in ALS patients were examined in the following manner. Patients who were definitely diagnosed to have clinically probable ALS or higher according to the Revised El Escorial Criteria were observed throughout a period of two occurrences of hospitalization and ambulatory follow-up. Further, during the first hospitalization period, the overall clinical conditions of the patients were assessed and screened, using the functional rating scale, Appel score, Norris scale, Neurophysiological index, and the like (Table 1).

TABLE 1

Stages of ALS diseases, and examination criteria for patients with ALS (based on Revised El Escorial Criteria of ALS)

Clinically Definite ALS: when all of the upper motor neuron signs and lower motor neuron signs are present in three or more regions.
Clinically Probable ALS: when all of the upper motor neuron signs and lower motor neuron signs are present in at least two regions, with the former being rostral to the latter
Clinically Probable-Laboratory-supported ALS: when the upper motor neuron signs and lower motor neuron signs are present in one region, or when the upper motor neuron signs alone are present in one region, with the electromyogramic findings being applicable to the electromyogram criteria in two or more limbs in both cases
Clinically possible ALS: when the upper motor neuron signs and lower motor neuron signs are present in one region, when the upper motor neuron signs alone are present in two or more regions, or when the lower motor neuron signs are rostral to the upper motor neuron signs
Clinically Suspected ALS: when definite lower motor neuron signs are present, or when the diagnosis of ALS could not be regarded as sufficiently certain to include the patient in a research study Example 2

Isolation of Bone Marrow-Derived Mesenchymal Stem Cells from Bone Marrow of Patient, and ex vivo Culture of the Cells 30 mL of the bone marrow was collected from the posterior superior iliac spine (PSIS) of a patient using a Jamshidi needle, and transferred into a sterile tube that had been treated with heparin. The bone marrow in the tube was then transported into a clean room, and the subsequent procedures were carried out. The tube containing the bone marrow was centrifuged at 700×g for 10 minutes at room temperature, and about 10 mL of the plasma was separated, and stored for stability test. 20 mL of the remaining bone marrow was diluted with DMEM (Dulbecco's Modified Eagle's Medium, Gibco) at 1:3, layered on the top of a Ficoll-Paque™ PREMIUM (density: 1.077 g/mL, GE Healthcare), and then centrifuged at 400×g for 30 minutes at room temperature. The mononuclear cell layer was separated, further added with DMEM, and then centrifuged at 400×g for 5 minutes at room temperature to obtain the mononuclear cells. The obtained mononuclear cells were centrifuged at 400×g for 5 minutes at room temperature, and washed using DMEM, which were repeated twice. The mononuclear cells after washing were put into a culture flask (175 cm$^2$) with DMEM(D)/F12 (Gibco) (referred to as 'D/F12+F+5% CS', hereinafter) containing MSCGM (Cambrex) or a self-developed medium (insulin (10 ng/mL), hydrocortisone (10 nM), EGF (10 ng/mL), and 5% human umbilical cord serum (referred to as 'CS', hereinafter), and cultured at 37° C. with 5% $CO_2$ for 5 days. After 5 days, the medium was exchanged with a fresh medium, thereby removing the cells which had not been adhered to the bottom of the culture flask. Thereafter, the medium was exchanged every 3 days, and subcultured to expand the cells. Upon passaging of the cells, the cells which had been adhered to the bottom of the culture flask were removed using 0.125% Trypsin-EDTA (Gibco).

Example 3

Ex vivo Culture of Bone Marrow-Derived Mesenchymal Stem Cells

In order to determine the viability of the bone marrow-derived mesenchymal stem cells obtained in the method as in Example 2, the cells were cultured ex vivo using various solutions. The cells were cultured in each of the culture solution of PBS, normal saline, plasma, and cerebrospinal fluid for 5 days, and the survival rate of the cells was determined daily at time points of 2 hrs, 6 hrs, and 24 hrs for 5 days. The results are illustrated in FIG. 1.

Generally, the survival rate was highest at 6 hrs, and then decreased over the time. Based on the survival rate at 24 hrs, the survival rate in PBS was higher than that in normal saline, the survival rate in plasma was higher than that in PBS, and the survival rate in cerebrospinal fluid was higher than that in plasma. Totally, the survival rate in plasma or cerebrospinal fluid was higher than that in normal saline or PBS. In particular, the survival rate in cerebrospinal fluid was even higher than those in the other solutions (FIG. 1).

Example 4

MSCs Treatment in Amyotrophic Lateral Sclerosis Mouse Model (SOD1 Mutant Transgenic Mouse Model)

The amyotrophic lateral sclerosis mouse models (B6SJL-Tg(SOD1-G93A)1Gur/J mice) were purchased from Jackson Laboratory (Bar Harbor, Me., USA) at an age of 4 weeks and were bred until they became 12 weeks old. The MSCs as prepared in Example 2 were washed with D-FBS (Dulbecco's Phosphate-buffered Salines, Gibco) three times ($10^3$ cells/g), thereby separating the cell layer. The obtained and washed MSCs were mixed with cerebrospinal fluid (CSF), put into a sterilized syringe, and then intrathecally injected into mice. The MSCs were injected at an interval of 2 weeks, and the animals in the control group were injected with physiological saline at an interval of 2 weeks during the same period. The symptoms of amyotrophic lateral sclerosis (early period: hands and feet shaking, cramping of muscles, and hyperreflexia; middle period: muscle weakness in arms and legs; and late period: myoparalysis in arms and legs, and muscle atrophy) were observed for comparison. Further, the mice were also subjected to periodical assessment for the change in motor ability using a Rotarod (Ugo Basile; Comerio-Varese, Italy). Starting from one week before administration, the mice were trained to be adapted to the rotarod machine. As the indices to be measured, the amount of time for the mice to stay on the rotarod, the number of rotations made at the time of falling, and the like were used. Each group consists of five mice, and measurements were made, at the time when the symptoms such as hands and feet shaking, cramping of muscles, hyperreflexia and the like, which are the initial symptoms of amyotrophic lateral sclerosis, were exhibited for the first time, being taken as the starting point for manifestation of symptoms, and the time when the mice could not spontaneously stand up from the ground within 30 seconds, taken as the end point. After taking the measurements for the time period, the mice were sacrificed. Also, changes in the body weight of the mice were measured periodically.

The results are shown in FIG. 2, indicating that in an assessment of the motor ability, the group of mice administered with MSCs showed enhanced motor ability, compared with the group of mice not administered, with the enhancement approaching about 30%, and the survival rate also increased to 10 days or longer.

INDUSTRIAL APPLICABILITY

The composition for treating motor neuron diseases using mesenchymal stem cells according to the present invention is effective in the treatment of motor neuron diseases, particularly amyotrophic lateral sclerosis (ALS).

The invention claimed is:
1. A method for treating motor neuron diseases, comprising intrathecally administering to an individual in need thereof an effective amount of a composition comprising mesenchymal stem cells, wherein the motor neuron disease is amyotrophic lateral sclerosis ("ALS"), progressive bulbar palsy ("PBP"), primary lateral sclerosis ("PLS"), or progressive muscular atrophy ("PMA"), wherein the mesenchymal stem cells express CD105 (SH2), CD29, CD44, and CD73 at 95% or more, express CD166 at 90% or more, express CD34, CD45, and HLA-DR at 5% or less, and express CDIa, CD14, CD31, and CD80 at 10% or less, and wherein mesenchymal stem cells are contained in an amount of 1×104 to 5×106 cells/ml in the composition, and wherein the individual exhibits enhanced motor ability.
2. The method according to claim 1, wherein the composition further comprises a diluent.
3. The method according to claim 2, wherein the diluent is any one of normal saline, PBS, HBSS, plasma, cerebrospinal fluid, and blood components.
4. The method according to claim 1, wherein the composition is used as an injectable preparation.

* * * * *